United States Patent [19]

Saven et al.

[11] Patent Number: 5,424,296
[45] Date of Patent: Jun. 13, 1995

[54] 2-HALO-2'-DEOXYADENOSINES AS THERAPEUTIC AGENTS AGAINST MALIGNANT ASTROCYTOMA

[75] Inventors: Alan Saven, San Diego; Lawrence D. Piro, La Jolla, both of Calif.

[73] Assignee: The Scripps Research Institute, La Jolla, Calif.

[21] Appl. No.: 48,111

[22] Filed: Apr. 15, 1993

[51] Int. Cl.⁶ .............................................. A61K 31/70
[52] U.S. Cl. .................................. 514/46; 536/27.63; 536/27.7
[58] Field of Search ........................ 514/46; 536/27.63

[56] References Cited

U.S. PATENT DOCUMENTS

| | | | |
|---|---|---|---|
| 4,719,295 | 1/1988 | Cook et al. | 536/27.62 |
| 4,826,823 | 5/1989 | Cook et al. | 514/46 |
| 5,106,837 | 4/1992 | Carson et al. | 514/46 |
| 5,310,732 | 5/1994 | Carson et al. | 514/46 |

OTHER PUBLICATIONS

Hine, *Physical Organic Chemistry*, 2nd ed., McGraw–Hill Book Co., Inc., New York (1962) p. 87.
Avery et al., "Biochemical Pharmacology of 2–Chlorodeoxyadenosine in Malignant Human Hematopoietic Cell Lines and Therapeutic Effects of 2–Bromodeoxyadenosine in Combinations in Mice," *Cancer Research*, 49, 4972–4978 (1989).
Cory et al., "Leukemia L1210 Cell Lines Resistant to Ribonucleotide Reductase Inhibitors," *Cancer Research*, 48(4), 839–843 (1988).
T. Beardsley, "Trends in Cancer Epidemiology—A War Not Won," *Scientific American*, 270(1), 130–138 (1994).
Saven et al., "2-Chlorodeoxyadenoisine Dose Escalation in Nonhematologic Malignancies," *J. Clinical Oncology*, 11(4), 671–678 (1993).

*Primary Examiner*—Douglas W. Robinson
*Assistant Examiner*—L. Eric Crane
*Attorney, Agent, or Firm*—Welsh & Katz, Ltd.

[57] ABSTRACT

A process for the treatment of malignant astrocytoma in mammals is disclosed that utilizes a 2-halo-2'-deoxyadenosine derivative as the active treating agent.

8 Claims, No Drawings

2-HALO-2'-DEOXYADENOSINES AS THERAPEUTIC AGENTS AGAINST MALIGNANT ASTROCYTOMA

This invention was made with government support under Contract No. RR 00833 by the National Institutes of Health. The government has certain rights in the invention.

DESCRIPTION

1. Technical Field

This invention relates to a novel treatment for malignant astrocytoma. More particularly, this invention relates to a process for the treatment of malignant astrocytoma involving the administration of a 2-halo-2'-deoxyadenosine.

2. Background of the Invention

Histologically and prognostically, cerebral astrocytomas can be divided into low-grade and high-grade subtypes. Glioblastoma multiforme is a most malignant form of astrocytoma. The median survival time for patients with malignant astrocytomas is dismal, usually being less than six months.

Surgery and radiation therapy remain the mainstays of therapy. Aggressive surgical resection has been associated with an improved clinical outcome. Re-operation for recurrence can also be efficacious. Postoperative radiation therapy is of value for incompletely resected lesion, however, median survival duration remains less than 12 months.

A number of chemotherapeutic agents have been shown to have activity when combined with irradiation as adjuvant therapy. This is true of the nitrosoureas where there is increased time to tumor progression and a survival advantage. Unfortunately, this advantage is only very modest. For recurrent and progressive tumors, the results of nitrosourea-based combinations are dismal. High-dose combination chemotherapy achieves only transient responses and the toxicity is considerable.

2-Chlorodeoxyadenosine (2-CdA) is a deoxyadenosine analog that is resistant to adenosine deaminase. This drug is used extensively in the treatment of patients with hematologic neoplasms such as lymphoid neoplasms and with autoimmune hemolytic anemia. Piro et al., Blood 72:1069–1073 (1988); Carson, In: Purine and Pyrimidine Metabolism in Man, Plenum Publishing Corp., New York, pp. 427–431, 1989; Piro et al. Blood 72 (Suppl 1):220A, (1988) (Abstract); Saven et al., Blood 74:239A (1989); Kay et al. Blood 74:121A (1989); Piro et al., N. Engl. J. Med. 322:1117–1121 (1990); Carson et al., Proc. Natl. Acad. Sci. USA, 81:2232–2236 (1984). 2-CdA has also been used in the treatment of certain autoimmune diseases, particularly rheumatoid arthritis.

These hematologic disorders are all related in that the involved cells are lymphocytic or monocytic in origin. For example, hairy cell leukemia, against which 2-CdA is the treatment of choice, is a disease of B-lymphocytes. Rheumatoid arthritis, a disease of uncertain etiology, is known to involve both lymphocytes and monocytes.

2-CdA has also been used in the treatment of CML in blast crisis. In a Phase I trial of two patients, 2-CdA treatment led to a decrease in blast count in one patient, and a loss of detectable tumor in another patient. Carson et al., Proc. Natl. Acad. Sci. USA, 81:2232–2236 (1984). However, patients not in blast crisis; i.e., those suffering from the chronic phase of CML, were not examined in this study. The blast crisis of CML is characterized by the proliferation of cells of lymphoid origin and is an acute leukemia that has heretofore been thought to require a different type of treatment than does the chronic form of this leukemia.

Clinical and in vitro studies have therefore focussed primarily on the use of 2-CdA on diseases with lymphocytic or monocytic involvement.

The effect of 2-CdA on in vitro on cultured marrow and blood cells from normal patients has been reported [Petzer et al., Blood, 78:2583–2587 (1991)] in a study published after the work underlying this invention was well underway. Erythroid progenitor cells showed a dose-dependent sensitivity to 2-CdA, with that sensitivity decreasing as the stage of progenitor maturation increased. Primitive burst-forming unit-erythroid (pBFU-E) cells displayed an $IC_{50}$ value (i.e., the concentration required to inhibit 50 percent of growth) of 19 nanomoles (nmol) per liter (nM). Mature BFU-E (mBFU-E) cells displayed $IC_{50}$ values of 38 nM. The last progenitor cell in the erythroid pathway, colony forming unit-erythroid (CFU-E) cells, displayed $IC_{50}$ values of 56 nM. Colony forming unit-granulocyte macrophage (CFU-GM) cells, progenitor cells to granulocytes (including neutrophils, eosinophils and basophils) and macrophages, displayed an $IC_{50}$ value of 16 nM in that study.

In a conflicting report, growth of CFU-GM cells was enhanced by 23 percent to 35 percent when exposed to 1 nM or 10 nM 2-CdA. A reduction of 60 percent was noted at a 2-CdA concentration of 100 nM. Carson et al. Blood, 62:737–743, 1983.

Results obtained in clinical trials of 2-CdA on various diseases also conflict with regard to the effects of the drug on neutrophils. For example, treatment of chronic lymphocytic leukemia at serum levels less than 10 nM led, in most cases, to an increase in neutrophil count. Piro et al., Blood, 72:1069–1073 (1988). 2-CdA administered at 0.1 mg/kg per day over a 7 day period to patients with cutaneous T cell lymphoma showed that the neutrophils in these patients were more resistant to 2-CdA than their monocytes and lymphocytes. Carrera et al., J. Clin. Invest., 86:1480–1488 (1990).

However, treatment of hairy cell leukemia led to transient neutropenia, with granulocyte counts under 500 per microliter. This effect was particularly acute in patients who were already neutropenic. Beutler et al., Leuk. Lymphoma, 5:8 (1991).

Still further, in previously unreported results relating to treatment of patients with multiple sclerosis, granulocyte counts were substantially unchanged after several courses of treatments with 2-CdA at about 0.1 mg/kg/day over seven day treatment courses of continuous infusion.

In view of the positive results obtained using a 2-halo-2'-deoxyadenosine for treating hematologic disorders, and particularly hematologic neoplastic diseases, it was of interest to examine this group of chemotherapeutic agents in solid, non-hematologic cancers. The disclosures that follow illustrate the positive results obtained against one type of solid tumor, malignant astrocytoma, and the negative results obtained with malignant melanoma and renal cell carcinoma. A preliminary report of these results appeared in Saven et al., Proc. Am. Soc. Clin. Oncol., 11:299 (1992).

SUMMARY OF THE INVENTION

The present invention contemplates a process for treating malignant astrocytoma. The compound utilized in the present invention as the active ingredient is a 2-halo-2'-deoxyadenosine.

This process for treating malignant astrocytoma comprises administering to a host mammal having malignant astrocytoma a therapeutically effective amount of a substituted adenosine derivative dissolved or dispersed in a pharmacologically acceptable carrier or diluent. That adenosine derivative has a structure that corresponds to that of Formula I:

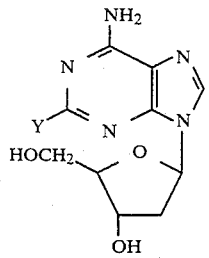

wherein Y is halogen. Y is preferably chloro.

A sufficient amount of one, or more, of the above compounds of Formula I, dissolved or dispersed in a pharmacologically acceptable carrier or diluent is used, to provide a therapeutically effective amount.

Depending upon the treatment modality, the administration of a compound of Formula I is typically carried out by providing about 0.04 to about 1.0 milligrams per kilogram of body weight, or more preferably by providing about 0.05 to about 0.20 mg/kg, or most preferably about 0.1 to about 0.20 mg/kg body weight per day. That treatment modality is typically repeated over a five to seven day course, and is typically repeated in cycles about every month until a maximal response of tumor size regression is observed.

In administering the treatment of the present invention, malignant astrocytomas of a host mammal with the disease are contacted with a composition containing a pharmacologically acceptable carrier that itself contains dissolved or dispersed therein a substituted adenosine derivative having a structure that corresponds to that of Formula I as an active ingredient or agent. The malignant astrocytomas are contacted in vivo by administration of the composition to a mammal such as a human.

A most preferred compound useful herein as active ingredient is 2-chloro-2'-deoxyadenosine (2-CdA) whose structure is shown below.

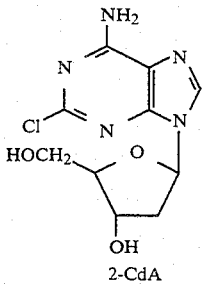

2-CdA

The present invention has several benefits and advantages.

A major advantage of the invention is that it provides a new, effective treatment for the malignant astrocytoma.

Another advantage of the invention is that its use avoids many of the potentially severe side effects of current drug therapies.

Still further benefits and advantages of the invention will be apparent to those skilled in the art from the description that follows.

DETAILED DESCRIPTION OF THE INVENTION

The present invention contemplates a process for treating malignant astrocytoma. It is believed that this process is the first report of a successful treatment of a solid tumor with a contemplated 2-halo-2'-deoxyadenosine. As will be discussed hereinafter, the positive effect found here as to malignant astrocytomas was not found with other solid tumors such as malignant melanoma and renal cell cancers.

In a contemplated process, a therapeutically effective amount of a Substituted adenosine derivative (2-halo-2'-deoxyadenosine) as an active ingredient dissolved or dispersed in a pharmaceutically acceptable carrier or diluent is administered to a host mammal having malignant astrocytoma. That substituted adenosine derivative has a structure that corresponds to that of Formula I:

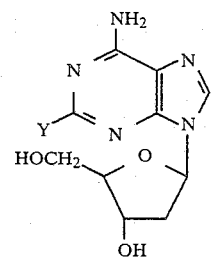

wherein Y is halogen.

In a preferred embodiment, Y is chloro.

The substituted adenosine derivative is present in the composition in an amount sufficient to provide a therapeutically effective amount (dose) over the period of contacting.

In the above formulas, and in all other formulas shown herein, hydrogen atoms on the purine and furanosidyl rings that are not needed to show conformation about a particular bond are not shown. Thus, the 7-position adenine hydrogen is not shown.

It is to be noted that the designation "halogen" used herein is meant to include fluorine, chlorine and bromine derivatives, and to exclude iodine derivatives, which are unstable and decompose, and astatine derivatives that are radioactive. Where specific halogen derivatives are intended, those compounds are named specifically.

A compound of Formula I dissolved or dispersed in or together with a pharmacologically acceptable carrier or diluent constitutes a composition useful in this invention.

Although a compound of Formula I can be administered as the pure chemical, it is preferred that it be administered as a pharmaceutical composition. In either event, it is administered in an amount sufficient to provide a therapeutically effective amount as is discussed hereinafter. Accordingly, the present invention utilizes a pharmaceutical composition comprising a therapeutically effective amount of a compound of Formula I hereinafter referred to as the "active ingredient" or "agent," dissolved or dispersed in a pharmacologically acceptable carrier or diluent.

A pharmaceutical composition is prepared by any of the processes well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction, such as gastric upset, dizziness and the like, when administered to a mammal such as a laboratory animal or human. The physiologically tolerable carrier can take a wide variety of forms depending upon the preparation desired for administration and the intended route of administration.

As an example of a useful composition, a compound of Formula I can be utilized in liquid compositions such as sterile suspensions or solutions, or as isotonic preparations containing suitable preservatives. Particularly well-suited for the present purposes are injectable media constituted by aqueous injectable isotonic and sterile saline or glucose solutions. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. One or more pharmaceutically acceptable preservatives can also be present in a composition.

The active agent can also be administered in the form of liposomes. As is known in the art, liposomes are generally derived from phospholipids or other lipid substances. Liposomes are formed by mono-or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

An agent of Formula I can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills are preferably provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose," as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

The synthesis and use of 2-halo-2'-deoxy-2'-arafluoroadenosine derivatives is also disclosed in U.S. Pat. No. 5,034,518, No. 4,918,179 and No. 4,751,221, whose disclosures are incorporated herein by reference.

It is particularly contemplated that the administering of a contemplated substituted adenosine derivative involve contact between the malignant astrocytoma and that adenosine derivative in vivo. Thus, a composition containing a compound of Formula I is administered in vivo to a mammal affected with such a disorder in amounts sufficient to provide a therapeutically effective amount of each drug to the mammal. The composition is maintained within the mammal host until its constituent components are eliminated by usual bodily processes.

The amount of a compound of Formula I present in a composition and used in a process as described above is a function of several variables, as is well known in the medicinal arts. Among those variables are the mammal treated, and the process of administration. Exemplary concentrations are illustrated hereinafter.

The amount administered is less than that which substantially impairs bone marrow functions (myelotoxicity) as determined by usual procedures. The above amount of a 2-halo-2'-deoxyadenosine derivative of Formula I in the composition is also an amount sufficient to provide about 0.04 to about 1.0 mg/kg of body weight of the treated host mammal per day, more preferably about 0.05 to about 0.20 mg/kg/day, and most preferably about 0.1 to about 0.20 mg/kg/day, when given in vivo. This amount is another way of defining a therapeutically effective amount that is particularly useful when a compound of Formula I is administered by infusion.

The molar plasma concentration of the compound of Formula I during treatment is preferably in the range of about 1 nanomolar (nM) to about 100 nM, particularly about 5 nM to about 50 nM, and more preferably about 10 nM to about 20 nM. Molarity of the 2-halo-2'-deoxyadenosine derivative in plasma of the treated (administered to) animal thus provides still another measure of a therapeutically effective dose from which the amount in a composition can be calculated. Concentrations in cerebral spinal fluid typically range in a dose-dependent manner between about 2 and 25 nmol/L when administration is by continuous intravenous infusion of 0.1–0.2 mg/kg/day.

It is to be understood that the above therapeutically effective dosages need not be the result of a single administration, and are usually the result of the administration of a plurality of unit doses. Those unit doses can in turn comprise portions of a daily or weekly dosage, and thus, the therapeutically effective dose is determined over the period of treatment (contacting).

It should be noted that continuous infusion at a rate designed to maintain the above described plasma concentration is particularly contemplated. That continuous infusion is typically carried out over a 5–7 day time period.

Duration of a particular treatment can also vary, depending on severity of the disease, and the hematological response obtained. Typical administration lasts for a time period of about 5 to about 14 days, with a 7-day time course being usual. Courses (cycles) of administration are also usually repeated at monthly intervals.

Courses (cycles) of treatment are usually continued until a maximum response or prohibitive toxicity is encountered. If, upon administration, a greater than 50 percent reduction in the pretreatment neutrophil or platelet count is noted, further treatment is withheld until both counts are greater than 75 percent of the pretreatment values, or $>1500$ neutrophils/$\mu$L and $>100\times 10^9$ platelets/L are noted.

A response to this treatment process can be determined according to the criteria proposed by Macdonald et al., *J. Clin. Oncol.*, 8:1277–1280 (1990). A complete response requires the disappearance of all enhancing tumor on consecutive CAT or MRI scans at least one month apart, off-steroids, and that the patient be neurologically stable or improved. A partial response is defined as a greater or equal to 50 percent decrease in size (largest cross-sectional area) of enhancing tumor on consecutive CAT or MRI scans at least one month apart, steroids stable or reduced, and that the patient be neurologically stable or improved. All other tumor responses were designated as no response.

Exemplary studies are illustrated hereinafter.

EXAMPLES

The present invention is further illustrated by the following examples which are not intended to limit the scope of the invention in any way.

Example 1: Phase I Study

Twenty-one patients having malignant astrocytoma (seven), malignant melanoma (twelve) or renal cell carcinoma (two) were enrolled in a Phase I study to assess the effects of different concentrations of 2-CdA upon their solid tumors.

The patients received continuous infusions of either 0.10, 0.15 or 0.20 mg/kg/day over seven day time periods in up to five monthly cycles. The patients with malignant astrocytomas received either 0.10 or 0.15 mg/kg/day; none receiving 0.20 mg/kg/day.

The 2-CdA used here was supplied by Ortho Pharmaceutical Corporation (Raritan, NJ) and was recrystalized before use [Carson et al., *Proc. Natl. Acad. Sci, USA,* 77:6865–6869 (1980)]. A solution at 1 mg/mL of pyrogen-free 2-CdA in sterile 0.9 percent NaCl was used as a stock solution that was diluted with further sterile 0.9 percent NaCl to prepare the final dosage in 100 mL. The finally diluted solution was infused through central venus access using an infusion pump device (Pharmacia Deltec Cadd) for out-patients, or infused by usual venus infusion for in-patients.

Each of the patients, except three (one renal cell carcinoma and two malignant melanoma) patients, had received a prior treatment. Each of the patients with malignant astrocytoma had been treated both surgically and with X-rays or by chemotherapy.

No alopecia, nausea, vomiting, cardiopulmonary, renal or hepatic toxicity occurred as a result of using this treatment process in any patient of this study. Myelosuppression was the principal toxic effect noted in this trial.

Myelosuppression (grades 3 or 4 neutropenia or thrombocytopenia) was more frequent in patients having had prior exposure to systemic chemotherapy. Thus, five of eight patients who developed myelosuppression had prior chemotherapy, whereas only two of thirteen patients without myelosuppression had prior chemotherapy. Four of the eight patients exhibiting myelosuppression had also received prior biologic therapies (interferon, interleukin-2, or lymphocyte-activated killer cells). Interestingly, all of the patients with previous biologic therapy treatment developed myelosuppression. Myelosuppression also increased with dosage of 2-CdA: 0.10 mg/kg/day=1/18 cycles; 0.15 mg/kg/day=5/22 cycles; and 0.20 mg/kg/day=$\frac{3}{4}$ cycles.

Two patients with malignant melanoma each of whom had had prior therapy exhibited delayed neurotoxicities. It is unknown whether those toxicities resulted directly from the 2-CdA treatment.

Two of the seven patients with malignant astrocytoma (GBM) exhibited myelosuppression. One patient had been previously treated with surgery as well as procarbazine, vincristine and carmustine. The other patient had received surgical and X-ray treatments and exhibited both neutropenia and thrombocytopenia after the fifth cycle with 2-CdA.

Two of the seven malignant astrocytoma patients (28.6 percent), one treated at 0.1 mg/kg/day and the other at 0.15 mg/kg/day responded with a median partial response that lasted for eight months. None of the patients with either malignant melanoma or renal cell carcinoma exhibited even a partial response to this treatment.

As to the two partial responses, patient No. 1 presented with a grade 2 astrocytoma that had previously been treated with multiple surgeries and irradiation. He received four cycles of 2-CdA at 0.10 mg/kg/day and achieved a partial response of seven months.

Coronal MRI scans of the brain of patient No. 1 with intravenous contrast (gadopenetrate dimeglumine) at presentation showed irregular and dense tumor enhancement identified in the splenium and posterior of the body of the corpus callosum with cephalad extension into the cingulate gyrus. A craniotomy defect was also noted. A coronal image at the identical slice after 2-CdA treatment showed resolution of tumor enhancement.

The second partial responding patient, patient No. 12, presented with GBM and had been previously treated with surgery and irradiation. This patient received five cycles of 2-CdA at 0.15 mg/kg/day, and achieved a partial response of nine months duration.

Axial spin echo MRI and sagittal T1-weighted images of the brain of patient No. 12 were also taken before and after treatment. An axial spin echo MRI image showed a 5-cm cystic neoplasm in the right posterior temporal lobe with extensive surrounding edema prior to treatment with 2-CdA. After that treatment, an identical slice showed complete regression of the edema and shrinkage of the cyst. Sagittal T1-weighted imaging before treatment also showed the cystic tumor with marked swelling of the entire temporal lobe. An identical slice after 2-CdA treatment showed complete regression of the temporal lobe swelling, with restoration of a normal sulcal pattern. The cyst was smaller in size and higher in signal intensity, possibly related to the decreasing water concentration with a secondary increase in the protein concentration.

Thus, this study, designed as a phase I study, illustrated that at least one, but not all, solid tumors can be treated with some success using a 2-halo-2'-deoxyadenosine. This study also showed that this active agent crosses the blood-brain barrier and can be used to provide a benefit to patients for whom other treatments were unsuccessful.

Example 2: Hard Shell Capsule

| Ingredient | Amount. mg /Capsule |
| --- | --- |
| 2-Bromo-9',1'-beta-2'-deoxyadenosine | 1 |
| Lactose, Spray Dried | q.s |
| Magnesium Stearate USP | 1–10 |

Example 3: I.V. Injectable Solution Concentrate

| Ingredient | Amount. % wt./vol. |
| --- | --- |
| 2-Fluoro-9,1'-beta-2'-deoxyadenosine | 0.1 |
| Benzyl Alcohol NF | 0.9 |
| Purified Water | 100.0 |

Example 4: Enteric Coated Adenine Derivative

Table 1 lists the components of a drug composition used in the present invention (Composition A) and an enteric coating composition (Composition B).

TABLE 1

| Ingredient | Weight |
| --- | --- |
| Composition A | |
| 2-Chloro-9,1'-beta-2'-deoxyadenosine | 67.0 |
| Polyvinylpyrrolidone | 1.3 |
| Modified Starch | 5.0 |
| Sodium Bicarbonate (anhydrous) | 20.0 |
| Citric Acid | 6.7 |
| | 100.0 |
| Composition B | |
| Chloroform | 66.4 |
| Methanol (anhydrous) | 15.4 |
| Cellulose Acetate Phthalate | 7.2 |
| Talc #127 U.S.P. | 7.3 |
| FD & C #5 Yellow | 1.0 |
| Diethyl Phthalate | 2.7 |
| | 100.0 |

The ingredients listed for Composition A are mixed, together with the slow addition of anhydrous isopropyl alcohol (700 ml per kg of Composition A) for about 9 to 15 minutes. The resulting blend is then segmented into tablets by extrusion. These segmented particles are dried in an oven at 35 degrees C for about 40 to about 48 hours. The dried granules are sized through a 14 mesh screen. Those segments that pass through the screen are compressed in a tablet machine to produce tablets about 4.8 mm in diameter and about 4 mm thick.

The dried tablets are then coated with the pH sensitive enteric coating composition (Composition B) in a pan employing about 0.45 liters of Composition B per kilogram of tablets to give a uniform coating weighing about 5.5% by weight of the final tablet. The wet coated tablets are then dried.

The foregoing description and the examples are intended as illustrative and are not to be taken as limiting. Still other variations within the spirit and scope of this invention are possible and will readily present themselves to those skilled in the art.

What is claimed is:

1. A process for treating malignant astrocytoma that comprises administering to a host mammal having malignant astrocytoma a therapeutically effective amount of a substituted adenosine derivative as an active ingredient dissolved or dispersed in a pharmacologically acceptable carrier, said adenosine derivative having a structure represented by the formula:

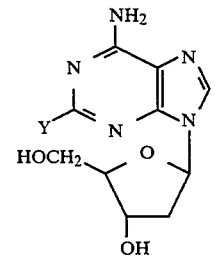

wherein Y is halogen.

2. The process of claim 1 wherein Y is chlorine.

3. The process of claim 1 wherein said administering provides said adenosine derivative in the plasma of said host mammal in an amount sufficient to provide an about 1 to about 100 nM concentration.

4. The process of claim 1 wherein said adenosine derivative is administered parenterally.

5. The process of claim 1 wherein said host mammal is a human.

6. A process for treating malignant astrocytoma that comprises administering to a human having malignant astrocytoma an amount of about 0.04 to about 1.0 milligrams per kilogram of body weight of a substituted adenosine derivative as an active ingredient dissolved or dispersed in a pharmacologically acceptable carrier, said adenosine derivative having a structure represented by the formula:

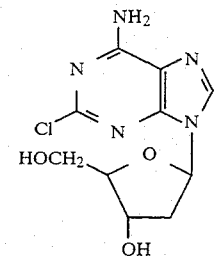

7. The process of claim 6 wherein said administering provides said adenosine derivative in the plasma of said host mammal in an amount of about 0.05 to about 0.20 milligrams per kilogram of host mammal body weight per day.

8. The process of claim 7 wherein said adenosine derivative is administered parenterally.

* * * * *